(12) United States Patent
Lee (10) Patent No.: US 8,257,379 B2
(45) Date of Patent: Sep. 4, 2012

(54) TISSUE STRUCTURE PERFORATION SYSTEM AND METHOD

(75) Inventor: Elaine Lee, Santa Clara, CA (US)

(73) Assignee: Kyphon SARL, Neuchatel (CH)

( * ) Notice: Subject to any disclaimer, the term of this patent is extended or adjusted under 35 U.S.C. 154(b) by 119 days.

(21) Appl. No.: 12/846,117

(22) Filed: Jul. 29, 2010

(65) Prior Publication Data

US 2012/0029543 A1  Feb. 2, 2012

(51) Int. Cl.
*A61B 17/32* (2006.01)

(52) U.S. Cl. .......................... 606/170; 606/186

(58) Field of Classification Search ............ 606/79, 606/116, 166, 167, 170, 138, 148, 190, 191, 606/183, 185–186; 83/546; 30/151, 152, 30/162, 163
See application file for complete search history.

(56) References Cited

U.S. PATENT DOCUMENTS

| | | | | |
|---|---|---|---|---|
| 4,705 A | * | 8/1846 | Tiemann | 606/183 |
| 4,717 A | * | 8/1846 | Ahrens | 606/183 |
| 361,533 A | * | 4/1887 | Little | 606/172 |
| 1,903,789 A | * | 4/1933 | Michaels | 30/304 |
| 2,197,650 A | * | 4/1940 | Piper et al. | 30/304 |
| 4,096,629 A | * | 6/1978 | Levine | 30/152 |
| 5,417,645 A | | 5/1995 | Lemmen | |
| 5,858,019 A | * | 1/1999 | Ashraf | 606/167 |
| 6,942,631 B2 | | 9/2005 | Hepburn et al. | |
| 7,300,412 B2 | | 11/2007 | Pappagallo et al. | |
| 2002/0123675 A1 | * | 9/2002 | Trautman et al. | 600/309 |
| 2004/0215197 A1 | * | 10/2004 | Smith et al. | 606/79 |
| 2007/0038181 A1 | * | 2/2007 | Melamud et al. | 604/158 |
| 2008/0167650 A1 | | 7/2008 | Joshi et al. | |
| 2010/0125266 A1 | * | 5/2010 | Deem et al. | 606/21 |
| 2011/0008413 A1 | | 1/2011 | Qiu et al. | |
| 2011/0059153 A1 | | 3/2011 | Zanella | |

* cited by examiner

*Primary Examiner* — Ryan Severson
*Assistant Examiner* — David Eastwood (57) ABSTRACT

A surgical treatment can involve creating a pattern of perforations in a tissue structure to allow lengthening of that tissue structure. For example, a pattern of perforations can be created in the transverse carpal ligament of a patient suffering from carpal tunnel syndrome (CTS) that allows the carpal ligament to lengthen slightly. This lengthening can relieve pressure on the median nerve, thereby reducing the symptoms of CTS while maintaining the structural integrity of the wrist. A surgical instrument for use in perforating a tissue structure (such as the transverse ligament) can be an elongate structure with one or more retractable blades. Such a tool can be used in either an open or minimally invasive procedure to create a desired pattern of perforations in the tissue structure.

6 Claims, 7 Drawing Sheets

TISSUE STRUCTURE PERFORATION SYSTEM AND METHOD

FIELD OF THE INVENTION

The invention relates to a system and method for minimally invasive surgical treatment of carpal tunnel syndrome.

BACKGROUND OF THE INVENTION

The carpal tunnel is an opening through the wrist into the hand that is formed by the carpal bones of the wrist on the bottom and the transverse carpal ligament on the top. The transverse carpal ligament is at the base of the wrist and crosses from one side of the wrist to the other. It is sometimes referred to as the carpal ligament or the flexor retinaculum.

The median nerve and flexor tendons of the hand run through the carpal tunnel. The median nerve rests on top of the flexor tendons, just below the carpal ligament. It gives sensation to the thumb, index finger, long finger, and half of the ring finger. It also sends a nerve branch to control the muscles of the thumb.

In general, carpal tunnel syndrome (CTS) develops when the tissues around the median nerve swell and press on the nerve. Early in the disorder, the process is reversible. Over time, however, the insulation on the nerves may wear away, and permanent nerve damage and severe loss of hand function may develop, along with pain, numbness, and tingling in the wrist, hand, and fingers. Only the little finger is unaffected by the median nerve.

Virtually all workers who use their hands and wrists repetitively are at risk for CTS, particularly if they work in cold temperatures and have factors or medical conditions that make them susceptible. For example, computer users/typists, workers in the meat and fish packing industries, airplane assemblers, and musicians are among those at very high risk for CTS. In addition, people who intensively cook, knit, sew, do needlepoint, play computer games, do carpentry, or extensively use power tools are likewise at increased risk for CTS.

Ideally, the early phases of carpal tunnel syndrome are treated before the damage progresses. A conservative approach to CTS, which may include corticosteroid injections and splinting, is typically the first step in treating this disorder. The conservative approach is most successful in patients with mild carpal tunnel syndrome. A concurrent regimen of physical therapy (e.g., a program of hand/wrist stretching and strengthening) may provide further benefits. In addition, alternative therapies such as ultrasound, nonsteroidal anti-inflammatory drugs (NSAIDs), ice/warmth, low-level laser therapy (LLLT), dietary modification, and acupuncture have been used in the treatment of CTS, with varying degrees of success.

For severe cases of CTS, surgery may be a more effective treatment option. Surgery is also more likely to be necessary for patients with underlying conditions such as diabetes. Even among patients with mild CTS, there is a high risk of relapse. Some researchers are reporting better results when specific exercises for carpal tunnel syndrome are added to the program of treatments.

Traditionally, in a CTS surgery, the carpal ligament is cut free ("released") from the median nerve, thereby relieving the pressure on the median nerve. The most common approach has been an open surgical procedure ("open carpal tunnel release" or "open release") performed in an outpatient facility, and is a straightforward and well-characterized procedure.

In recent years, more surgeons have adopted a "mini" open—also called short-incision—procedure. This surgery requires only a one-inch incision, but it still allows a direct view of the area (unlike endoscopy, which is viewed on a monitor). The mini-open approach may allow for quicker recovery while avoiding some of the complications of endoscopy, although few studies have investigated its benefits and risks. The recovery time in patients receiving the mini-open approach may be shorter than with the open approach, and results are generally the same.

Endoscopy for CTS is another less invasive procedure than standard open release. In an endoscopic release procedure, a surgeon makes one or two ½-inch incisions in the wrist and palm, and inserts one or two endoscopes (pencil-thin tubes). The surgeon then inserts a tiny camera and a knife through the lighted tubes. While observing the underside of the carpal ligament on a screen, the surgeon cuts the ligament to free the compressed median nerve.

Endoscopic release patients report less pain than those who had the open release procedure, and return to normal activities in about half the time. Nevertheless, at this time the best evidence available does not show any significant long-term advantages of endoscopy over open release in terms of muscle, grip strength, or dexterity. The endoscopic approach may even carry a slightly higher risk of pain afterward. This may be due to a more limited view of the hand with endoscopy. Concerns of irreversible nerve injury with endoscopic carpal tunnel release, when compared with open carpal tunnel release, exist because of this reduced visibility.

Regardless of the procedure, patients who have undergone conventional CTS surgery typically report some permanent loss of grip strength, a loss of lifting strength in the wrist/forearm and nagging loss of full range of motion of the hand and wrist after surgery. This is due to the severing of the carpal ligament. The purpose of the carpal ligament is to wrap around the hand and wrist and hold the many small bones of the hand and wrist securely together. The carpal ligament also maintains the flexor tendons in a path that enables the mechanical advantage necessary for strong grip strength and range of motion. These support capabilities are naturally diminished when the ligament is severed.

Accordingly, it is desirable to provide a system and technique for alleviating the symptoms of CTS while maintaining as much grip strength and/or range of motion of the hand and wrist.

SUMMARY OF THE INVENTION

By providing an elongated tool with one or more retractable blades, modification of a tissue structure via perforation can be performed to beneficially enable lengthening of that tissue structure. For example, the transverse carpal ligament can be lengthened in such a manner, thereby relieving pressure on the median nerve. In this manner, the painful and problematic symptoms of carpal tunnel syndrome (CTS) can be alleviated without fully severing the transverse carpal ligament, which in turn may minimize the loss of grip strength and/or hand and wrist range of motion associated with surgical treatments for CTS.

In some embodiments, a tissue perforator for treating CTS can include an elongate instrument having one or more retractable blades. The retractable blades allow for placement of the instrument alongside the transverse carpal ligament while minimizing the risk of injury to adjacent structures (e.g., the median nerve or flexor tendons, among others). The safety of this placement operation can be further enhanced by forming the elongate instrument with a distal region having one or more of a blunt tip, a tapered tip, a round tip, and/or a flexible (soft) tip.

The blades can take any form for perforating a ligament, such as sawtooth, shark tooth, conical point, or pyramid-shaped, among others. In addition, the blades can be arranged in any pattern that can provide an appropriate perforation pattern in the target ligament. For example, in various embodiments, the blades can be arranged in a single row (e.g., aligned with a longitudinal axis of the tissue perforator). In various other embodiments, the blades can be arranged in multiple rows or in a staggered array, to enhance the ability of the instrument to efficiently create the desired perforation pattern in the ligament. In yet other embodiments, the tissue perforator can incorporate or be paired with a clamp for forcibly pressing the ligament onto the exposed blades to ensure proper ligament perforation.

In some embodiments, the blades can be attached to a base structure in the elongate element, with a guard positioned over the blades. The guard can include one or more openings aligned with the blades to allow the blades to be controllably (selectably) exposed or hidden. In various embodiments, the blades can be fixedly attached to the base structure, such that moving the guard and base structure together or apart can cause the blades to be exposed or hidden, respectively. In various other embodiments, the blades can be rotatably coupled to the base structure and/or the guard, such that the blades can be rotated in a first direction to be deployed outside the guard, and rotated in a second direction to be retracted back into the guard. Various other deployment mechanisms will be readily apparent.

In various other embodiments, a procedure for treating problematic physical conditions can involve perforating a tissue structure to enable lengthening of that tissue structure. In various embodiments, the treatment of CTS can involve perforating the transverse carpal ligament with a pattern of openings. The pattern of perforations allows the carpal ligament to elongate, thereby relieving the pressure on the median nerve within the carpal tunnel. At the same time, because the ligament is not completely severed, the structural integrity of the wrist (carpal tunnel) is largely maintained. In some embodiments, an implant or external brace can be used to temporarily or permanently provide additional lengthening of the transverse carpal ligament.

The ligament perforation procedure can be performed either percutaneously or via open access. In some embodiments, the perforation can be performed using an instrument having one or more retractable blades. The instrument (with blades stowed) can be placed adjacent to the transverse carpal ligament, the blades can be deployed, and the ligament perforated using those blades. A desired pattern of perforations can be created by retracting the blades, repositioning the instrument, and then redeploying the blades to create additional perforations in the ligament at a different location.

The actual perforation of the carpal ligament can be performed by pressing, vibrating, and/or using a slight cutting motion of the blades against the carpal ligament. In other embodiments, the carpal ligament can be physically pressed on to the blades (e.g., via a clamping element used in conjunction with the tissue perforator) to ensure proper perforation of the ligament. The actions of pressing, vibrating, or cutting may be performed manually, with an automated or powered mechanism, or by a combination of methods.

As will be realized by those of skilled in the art, many different embodiments of a tissue perforator and/or methods of lengthening tissue structures such as the transverse carpal ligament via perforation are possible. Additional uses, advantages, and features of the invention are set forth in the illustrative embodiments discussed in the detailed description herein and will become more apparent to those skilled in the art upon examination of the following.

DETAILED DESCRIPTION

By providing an elongated tool with one or more retractable blades, modification of a tissue structure via perforation can be performed to beneficially enable lengthening of that tissue structure. For example, the transverse carpal ligament can be lengthened in such a manner, thereby relieving pressure on the median nerve. In this manner, the painful and problematic symptoms of carpal tunnel syndrome (CTS) can be alleviated without fully severing the transverse carpal ligament, which in turn may minimize the loss of grip strength and/or hand and wrist range of motion associated with surgical treatments for CTS.

Figure 1A:
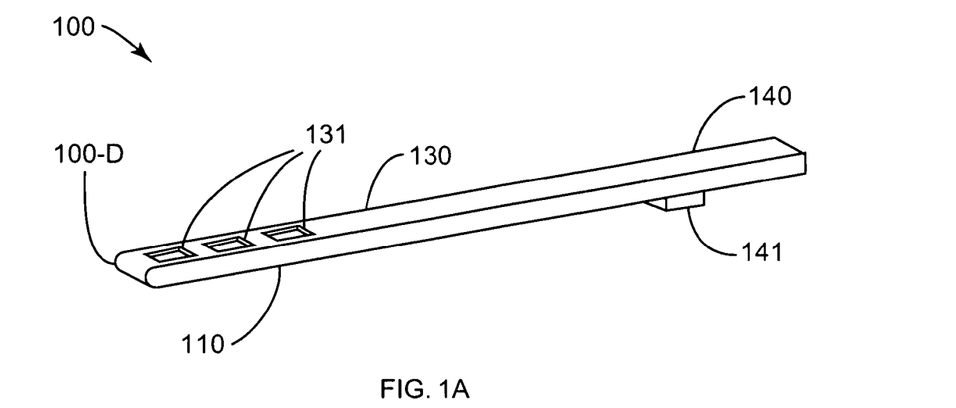
FIGS. 1A-1C show an exemplary tissue perforator with retractable blades.
Figure 1B:
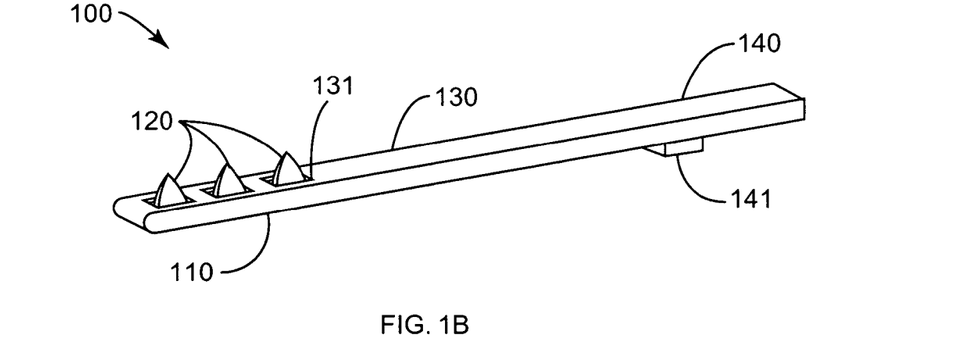

FIGS. 1A and 1B show an exemplary tissue perforator 100 that includes an elongate base 110 that extends from a handle (i.e., gripping area) 140 to a distal tip 100-D. In various embodiments, distal tip 100-D can be blunt, curved, narrowed, rounded, tapered, and/or otherwise shaped to minimize the chances of damage to surrounding tissue during use. As shown in FIG. 1A, tissue perforator 100 further includes a guard 130 that provides a relatively smooth exterior surface to minimize the risk of unintended tissue damage during placement and removal of tissue perforator 100 in a patient.

Guard 130 hides a set of blades 120 that are extended through openings 131 when actuated by actuator 141, as shown in FIG. 1B. When deployed in this manner, blades 120 can be used, for example, to perforate a tissue structure such as the transverse carpal ligament of a patient suffering from CTS, thereby allowing the ligament to lengthen and relieve at least some of the pressure on the median nerve (as described in greater detail below).

Note that actuator 141 can be any mechanical, electrical, or electronic trigger for controllably hiding/exposing blades 120, such as a lever, a slide, a button, a switch, a knob, a sensor, or even simply an area for squeezing guard 130 towards base 110. Various other actuator implementations will be readily apparent.

Figure 1C:
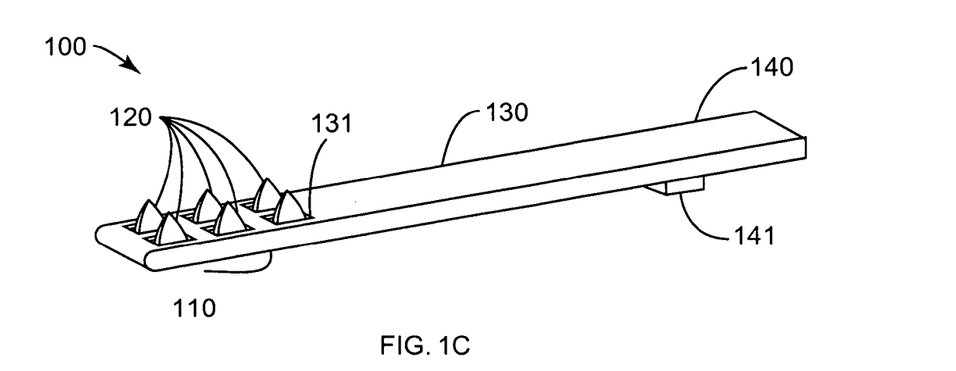

Note further that while a single row of three blades 120 is depicted for exemplary purposes, a tissue perforator can include any number and any arrangement of blades 120. For example, in various embodiments, tissue perforator 100 can include multiple rows of blades 120 (as shown in FIG. 1C), either aligned or staggered. In various other embodiments, tissue perforator 100 can include a row of blades that is not aligned with the longitudinal axis of tissue perforator 100. Various other blade configurations will be readily apparent.

Note further that while blades 120 are depicted as having a "shark tooth" profile for exemplary purposes, in various other embodiments, blades 120 can take any profile. For example, in various embodiments, blades 120 can be diamond-shaped, chisel-shaped, or any other shape. Furthermore, blade 120 can be any feature for creating a perforation in a tissue structure (e.g., a ligament, nerve sheath, tendon, or even the skin), including a needle or cone tip, a vibrating element (e.g., an ultrasonic scalpel), or an electrosurgical cutting tip. Note also that in various embodiments, blades 120 can be configured to enable the option of completely severing (releasing) the ligament, depending on how perforator 100 is manipulated.

Figure 2A:
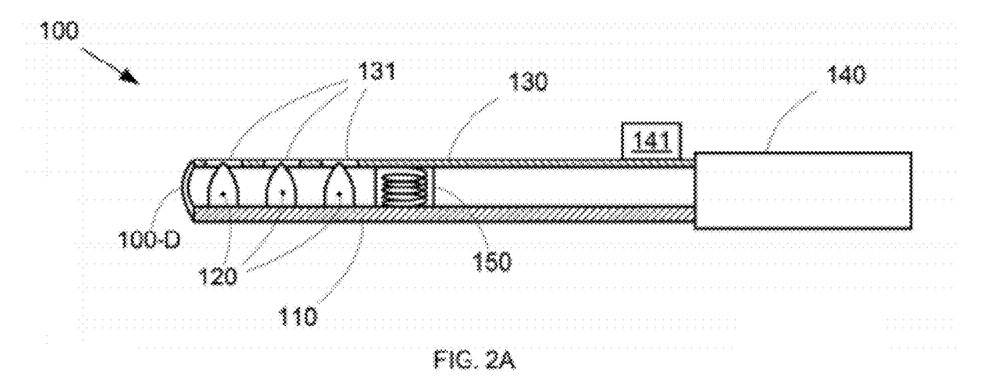
FIGS. 2A-2E show an exemplary blade deployment mechanism for a tissue perforator.
Figure 2B:
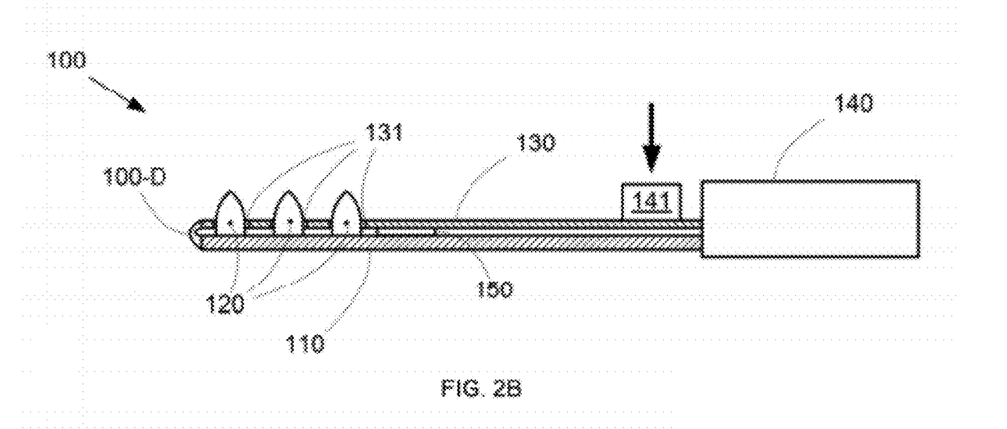

FIG. 2A shows an exemplary embodiment of a deployable/retractable blade mechanism for tissue perforator 100. In FIG. 2A, blades 120 are fixedly attached to base 110, and guard 130 is movable with respect to base 110. When base 110 and guard 130 are far enough apart, blades 120 are hidden beneath the surface of guard 130. By moving guard 130 and base 110 closer to each other (e.g., by pressing or squeezing the region of actuator 141), blades 120 can be made to protrude through openings 131 of guard 130, as shown in FIG. 2B.

Note that in some embodiments, distal tip 100-D of tissue perforator 100 can include a flexible element that maintains a blunt distal profile even as base 110 and guard 130 are moved relative to one another. In various other embodiments, base 110 and/or guard 130 can be at least partially contained with an external housing that provides a smooth exterior for tissue perforator 100.

Figure 2C:
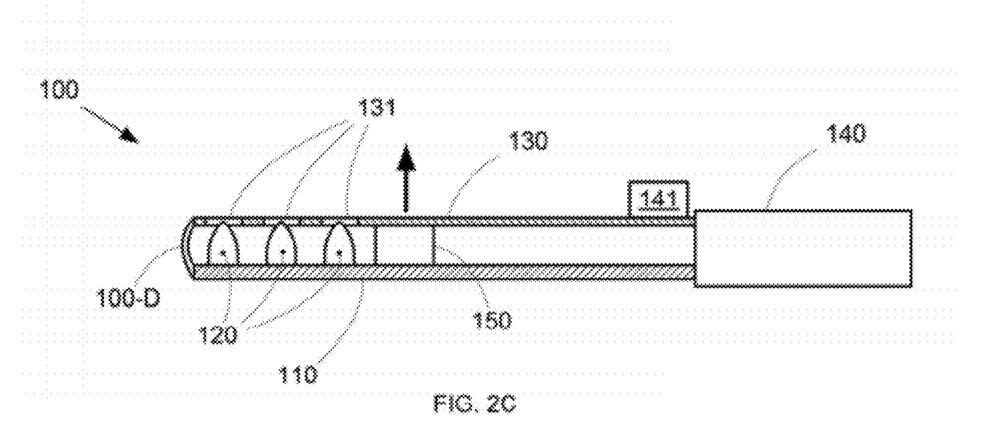

Tissue perforator 100 can further include a resilient element 150 (e.g., a spring or other elastic element) that biases base 110 and guard 130 apart, thereby causing blades 120 to be retracted when pressure is released at actuator 141, as shown in FIG. 2C. Note that in various other embodiments, the need for resilient element 150 can be eliminated by having the construction of tissue perforator inherently bias base 110 and guard 130 apart (e.g., a "tweezers" construction) or by having a manual retraction mechanism (e.g., scissor grips).

Figure 2D:
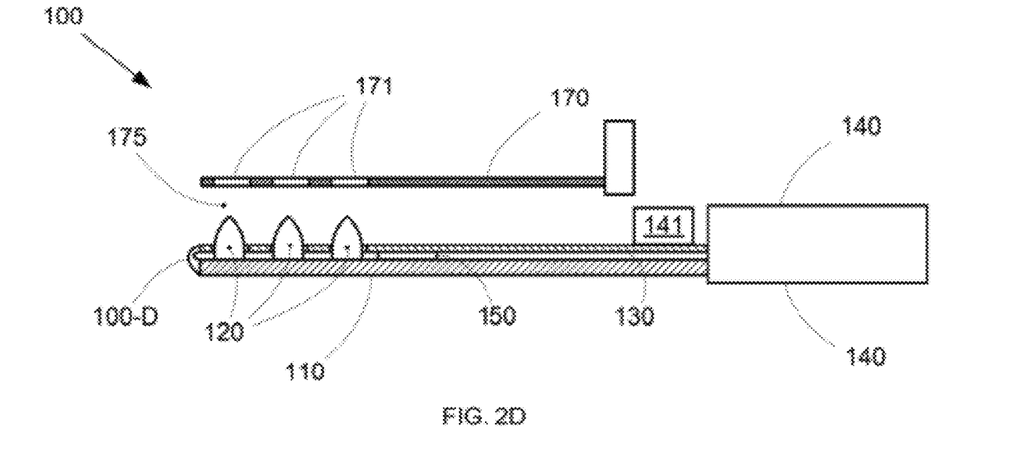
Figure 2E:
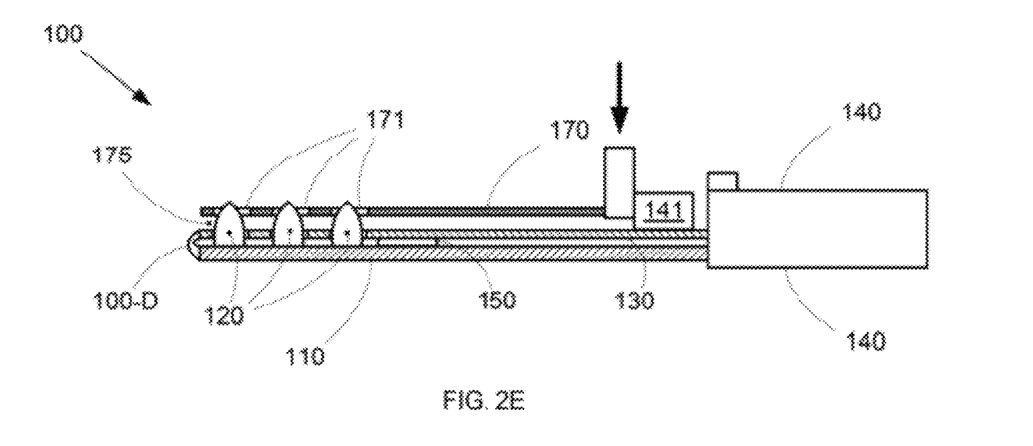

Note that in various other embodiments, additional elements can be provided for enhancing the ligament perforation procedure. For example, in FIG. 2D, tissue perforator 100 further includes a clamp 170 that includes openings 171 aligned with blades 120. During a surgical procedure, the target tissue structure can be placed in a gap 175 between deployed blades 120 and clamp 170. Clamp 170 can then be used to press the tissue structure onto blades 120 as shown in FIG. 2E, thereby ensuring proper perforation of the ligament. Note that clamp 170 can be integrated with, or discrete from, tissue perforator 100.

Figure 3A:
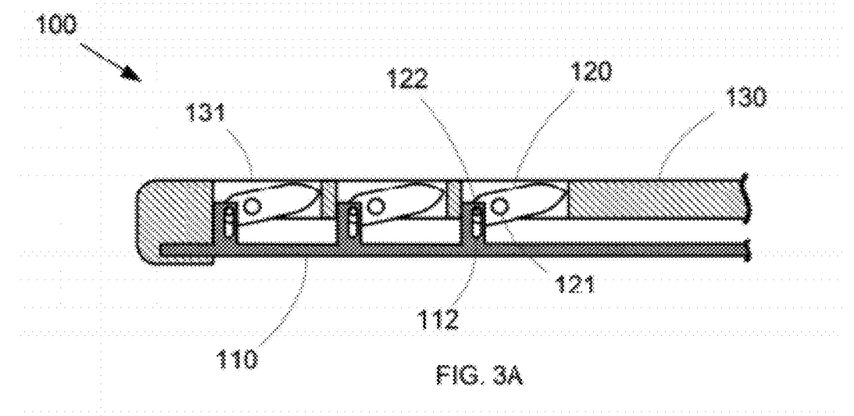
FIGS. 3A-3C show another exemplary blade deployment mechanism for a tissue perforator.

FIG. 3A shows another exemplary embodiment of a deployable/retractable blade mechanism for tissue perforator 100. In FIG. 3A, blades 120 are pivotally mounted in tissue perforator 100 (e.g., connected to guard 130 via rotational couplings 121). Rotational couplings 121 can include any mechanisms that allow blades 120 to rotate (e.g., a pin/hole, bushing, and/or rivet, among others).

Blades 120 are also coupled to base 110 via a linkage that allows base 110 to control the rotational orientation of blades 120. For exemplary purposes, each of those linkages is depicted as a pin 122 on blade 120 positioned within a slot 112 on base 110. However, various other linkage constructions will be readily apparent.

Figure 3B:
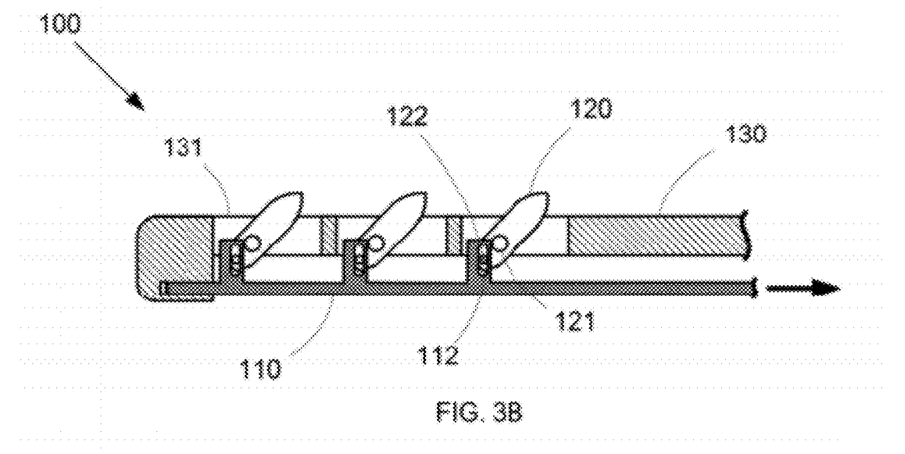
Figure 3C:
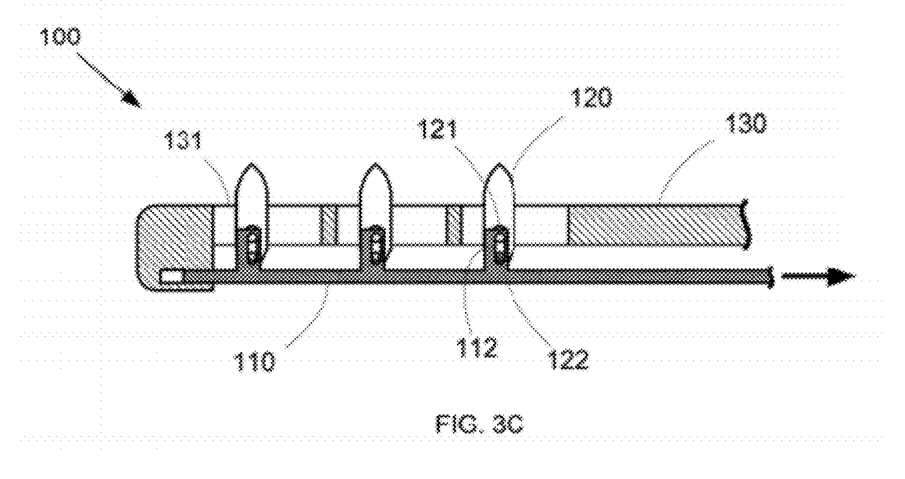

Initially, blades 120 are oriented such that they remain retracted within guard 130 (i.e., hidden beneath the surface of guard 130), as shown in FIG. 3A. As base 110 is moved relative to guard 130, slots 112 pull pins 122 on blades 120, causing them to rotate upwards and out of openings 131 as shown in FIG. 3B. Continued movement of base 110 relative to guard 130 ultimately results in full deployment of blades 120, as shown in FIG. 3C. Subsequent retraction of blades 120 can be accomplished by movement of base 110 in the opposite direction relative to guard 130.

Note that while longitudinal motion of base 110 relative to guard 130 to deploy/retract blades 120 is depicted and described for exemplary purposes, in various other embodiments movements an any other direction can be used to control the rotational orientation of blades 120. For example, base 110 could be moved rotationally with respect to guard 130 (e.g., in a scissoring configuration) to deploy/retract blades 120. Various other arrangements will be readily apparent.

FIGS. 4A-4E show an exemplary procedure involving the surgical lengthening of a tissue structure for treating CTS, in which the painful and problematic symptoms of the condition can be relieved without taking the drastic step of severing the transverse carpal ligament. Note that while a CTS treatment procedure is depicted and described for exemplary purposes, the underlying perforation technique can be applied to any tissue structure where lengthening of that tissue structure would be beneficial.

Figure 4A:
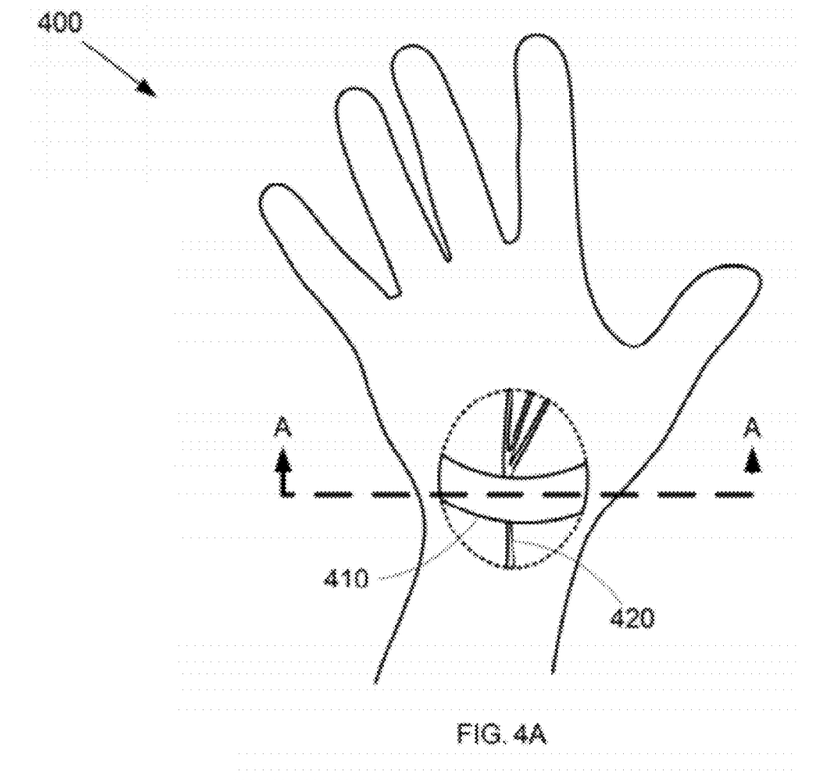
FIGS. 4A-4E show an exemplary treatment procedure for carpal tunnel syndrome using a tissue perforator.

FIG. 4A shows a cutaway view of a hand 400 that shows the position of the median nerve 420 running beneath the transverse carpal ligament 410. Note that hand 400 would typically be the hand of a patient suffering from CTS, with the below-described procedure being the surgical CTS treatment. However, in various other embodiments, hand 400 could be the hand of a cadaver, or simply a model hand (with the procedure being performed for training/instructional purposes).

Figure 4B:
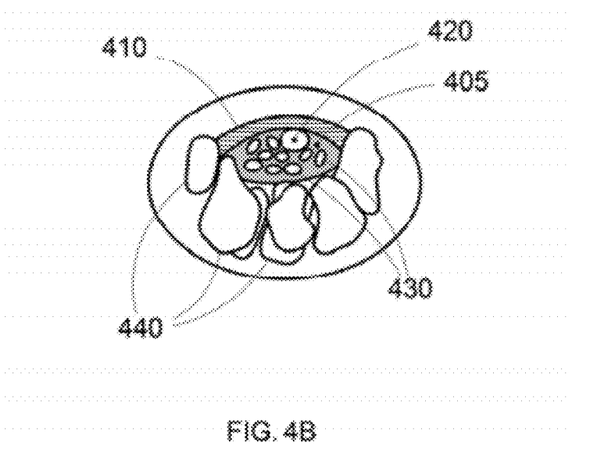

Sectional view A-A shown in FIG. 4B depicts the carpal tunnel 405 formed by the carpal ligament 410 and the wrist (carpal) bones 440. Within carpal tunnel 405 run median nerve 420 and flexor tendons 430, which bend the fingers and thumb of hand 400. Impingement of carpal ligament 410 on median nerve 420 as shown in FIG. 4B causes CTS and its concomitant symptoms.

Figure 4C:
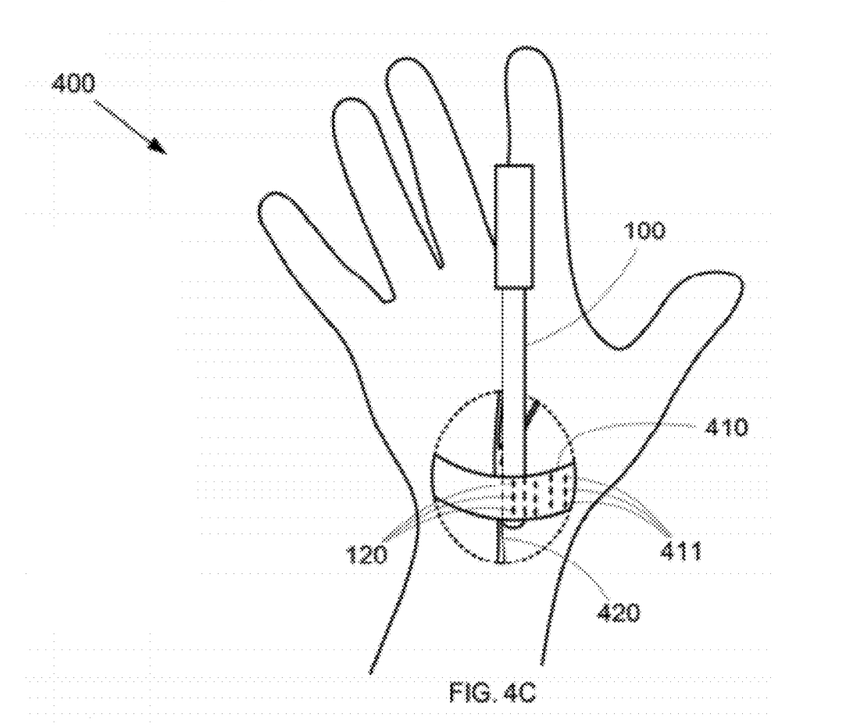

To relieve those symptoms, a series of perforations 411 can be made in transverse carpal ligament 410 as shown in FIG. 4C. In some embodiments, a fixed blade instrument (i.e., an instrument without retractable blades) can be used to create perforations 411. However, in various other embodiments, tissue perforator 100 as described with respect to FIGS. 1A-1B, 2A-2E, and 3A-3C can be used. In particular, tissue perforator 100 can be placed adjacent to carpal ligament 410, after which blades 120 can be deployed and used to create perforations 411.

Note that in some embodiments, tissue perforator 100 can be placed beneath carpal ligament 110 (i.e., within the carpal tunnel) so that blades 120 are deployed away from median nerve 420. However, in various other embodiments, tissue perforator 100 can be placed on top of carpal ligament 410 (i.e., blades 120 are deployed towards the interior of the carpal tunnel), so long as care is taken to prevent injury to median nerve 420 and any other structures within the carpal tunnel (e.g., via shielding or careful placement).

Note further that the slim, elongated profile of tissue perforator 100 lends itself to use in a percutaneous procedure (i.e., forming perforations 411 via a small incision in the skin such as in an endoscopic or mini-open procedure), although it can also be used in an open procedure. In various embodiments, tissue perforator 100 can be used in conjunction with endoscopic, fluoroscopic, and/or other visualization tools.

Figure 4D:
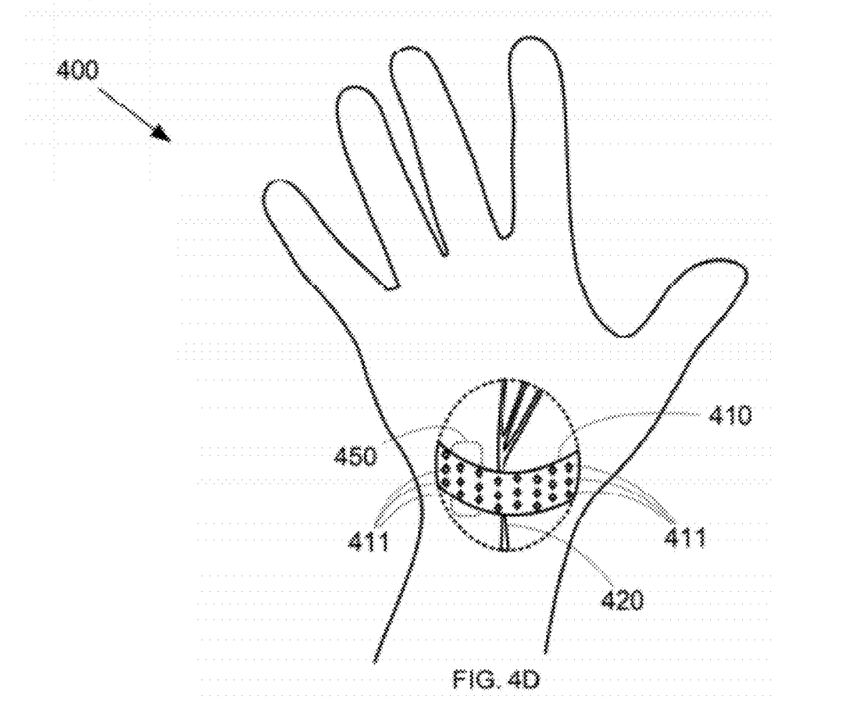

After a set of perforations 411 has been created, blades 120 can be retracted, tissue perforator 100 can be repositioned, and blades 120 can then be re-deployed to create a new set of perforations 411. This process can be repeated until a desired pattern of perforations 411 is created in transverse carpal ligament 410, as shown in FIG. 4D.

Perforations 411 can allow transverse carpal ligament 410 to lengthen slightly, without significantly diminishing the overall structural integrity of ligament 410. Essentially, perforations 411 "open up" to increase the length of transverse carpal ligament 410. Increasing the size and/or number of perforations 411 can further increase the lengthening of carpal ligament 410.

Figure 4E:
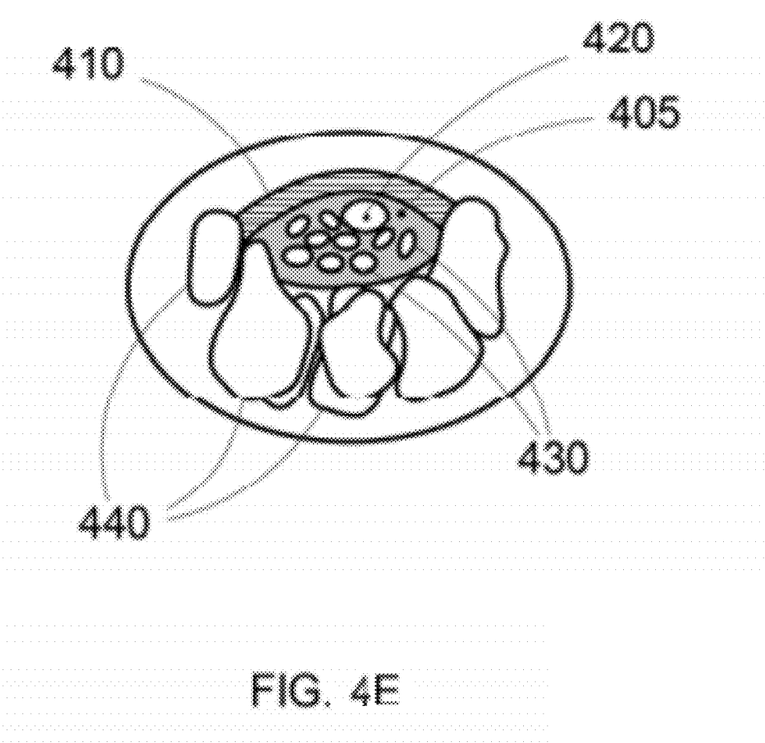

This lengthening of carpal ligament 410 provides more space within carpal tunnel 405, as shown in FIG. 4E. In various embodiments, the lengthening of carpal ligament 410 can be assisted or enhanced through the use of an optional temporary, resorbable, or permanent implant(s) 450 within carpal tunnel 405 and/or braces/splints outside of carpal tunnel 405, as indicated in FIG. 4D.

In any event, the additional space created within carpal tunnel 405 by the lengthening of carpal ligament 410 results in reduced or eliminated impingement of median nerve 420 by carpal ligament 410, and the pain, tingling, and/or numbness associated with CTS can be reduced or eliminated. At the same time, because transverse carpal ligament 410 is not completely severed, the overall structure of the wrist is not significantly compromised, and the problems associated with conventional carpal tunnel release surgery can be avoided.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A surgical instrument comprising:
    a plurality of blades;
    an elongate body, the elongate body comprising a guard comprising a plurality of openings, the guard being configured for controllably hiding and exposing the plurality of blades, the plurality of blades being coupled to a distal region of the elongate body, the distal region of the elongate body having a blunt distal tip, wherein the plurality of blades is exposed through the plurality of openings; and
    a clamping element for clamping against the plurality of blades when the plurality of blades is exposed by the guard.

2. The surgical instrument of claim 1, wherein the plurality of blades is arranged in a single row aligned with a longitudinal axis of the elongate body.

3. The surgical instrument of claim 1, wherein the plurality of blades are arranged in a plurality of rows, each of the plurality of rows being aligned with a longitudinal axis of the elongate body.

4. The surgical instrument of claim 1, wherein the plurality of blades are fixedly coupled to a surface of the elongate body, wherein the surface of the elongate body and the guard are moveable with respect to one another, wherein moving the surface of the elongate body and the guard towards each other exposes the plurality of blades through the plurality of openings.

5. The surgical instrument of claim 4, further comprising a resilient element, the resilient element biasing the surface of the elongate body and the guard apart.

6. The surgical instrument of claim 1, wherein the clamping element comprises a second plurality of openings substantially aligned with the plurality of openings of the guard.

* * * * *